(12) United States Patent
Sansoucy

(10) Patent No.: US 10,058,676 B2
(45) Date of Patent: Aug. 28, 2018

(54) MEDICAL CATHETER HAVING A DESIGN PROVIDING LOW RECIRCULATION AND REVERSIBILITY

(75) Inventor: Michael R. Sansoucy, Wrentham, MA (US)

(73) Assignee: Covidien LP, Mansfield, MA (US)

( * ) Notice: Subject to any disclaimer, the term of this patent is extended or adjusted under 35 U.S.C. 154(b) by 1374 days.

(21) Appl. No.: 12/894,269

(22) Filed: Sep. 30, 2010

(65) Prior Publication Data

US 2011/0077577 A1    Mar. 31, 2011

Related U.S. Application Data

(60) Provisional application No. 61/289,073, filed on Dec. 22, 2009, provisional application No. 61/247,101, filed on Sep. 30, 2009.

(51) Int. Cl.
*A61M 25/00*    (2006.01)

(52) U.S. Cl.
CPC ......... *A61M 25/003* (2013.01); *A61M 25/007* (2013.01); *A61M 25/0032* (2013.01); *A61M 2025/0031* (2013.01); *Y10T 29/49826* (2015.01)

(58) Field of Classification Search
CPC .............. A61M 25/003; A61M 25/007; A61M 25/0032; A61M 205/00312
USPC ...... 604/43, 6.16, 29, 93.01, 102.01–102.03, 604/118–121
See application file for complete search history.

(56) References Cited

U.S. PATENT DOCUMENTS

| 701,075 A | 5/1902 | McCully |
| 2,541,691 A | 2/1951 | Eicher |
| D208,838 S | 10/1967 | St. Amand |

(Continued)

FOREIGN PATENT DOCUMENTS

| CA | 2 326 941 | 10/1976 |
| CA | 2 389 227 | 10/2001 |

(Continued)

OTHER PUBLICATIONS

European Search Report EP 10 18 4012 dated Oct. 28, 2011.

(Continued)

*Primary Examiner* — Nathan R Price
*Assistant Examiner* — Weng Lee
(74) *Attorney, Agent, or Firm* — Kenneth Collier; Jessica Kwak Rauckman

(57) ABSTRACT

The present disclosure relates to a medical catheter including an elongate catheter member defining a longitudinal axis and having a proximal end, a distal end, an outer wall, and first and second internal lumens. The outer wall of the catheter member includes a first opening in fluid communication with the first internal lumen to facilitate the establishment of a first flow stream, and a second opening in fluid communication with the second internal lumen to facilitate the establishment of a second flow stream. Each of the first and second openings includes proximal and distal tapered portions that are connected by an intermediate portion having a constant transverse dimension. The configurations, dimensions, and positioning of the first and second openings optimizes separation of the first flow stream from the second flow stream in order to reduce the likelihood of recirculation between the first and second internal lumens.

20 Claims, 8 Drawing Sheets

(56) References Cited

U.S. PATENT DOCUMENTS

| | | |
|---|---|---|
| 3,926,705 A | 12/1975 | Todd |
| 4,134,402 A | 1/1979 | Mahurkar |
| D254,270 S | 2/1980 | Ziegler |
| 4,403,983 A | 9/1983 | Edelman et al. |
| D272,651 S | 2/1984 | Mahurkar |
| 4,443,333 A | 4/1984 | Mahurkar |
| 4,493,696 A | 1/1985 | Uldall |
| 4,568,329 A | 2/1986 | Mahurkar |
| 4,583,968 A | 4/1986 | Mahurkar |
| 4,601,697 A | 7/1986 | Mammolenti et al. |
| 4,604,379 A | 8/1986 | Twardowski et al. |
| 4,619,643 A | 10/1986 | Bai |
| 4,626,240 A | 12/1986 | Edelman et al. |
| 4,643,711 A | 2/1987 | Bates |
| D289,682 S | 5/1987 | Dragan |
| 4,675,004 A | 6/1987 | Hadford et al. |
| 4,682,978 A | 7/1987 | Martin |
| 4,687,471 A | 8/1987 | Twardowski et al. |
| 4,692,141 A | 9/1987 | Mahurkar |
| D292,285 S | 11/1987 | Dragan |
| 4,769,005 A | 9/1988 | Ginsburg et al. |
| 4,770,652 A | 9/1988 | Mahurkar |
| 4,772,268 A | 9/1988 | Bates |
| 4,772,269 A | 9/1988 | Twardowski et al. |
| D298,461 S | 11/1988 | Manno |
| 4,795,439 A | 1/1989 | Guest |
| 4,808,155 A | 2/1989 | Mahurkar |
| 4,808,156 A | 2/1989 | Dean |
| 4,842,582 A | 6/1989 | Mahurkar |
| 4,894,057 A | 1/1990 | Howes |
| 4,895,561 A | 1/1990 | Mahurkar |
| 4,897,079 A | 1/1990 | Zaleski et al. |
| 4,904,238 A | 2/1990 | Williams |
| 4,961,809 A | 10/1990 | Martin |
| D312,872 S | 12/1990 | Mähl |
| 4,995,865 A | 2/1991 | Gahara et al. |
| 5,009,636 A | 4/1991 | Wortley et al. |
| 5,015,184 A | 5/1991 | Perry et al. |
| 5,035,399 A | 7/1991 | Rantanen-Lee |
| 5,041,083 A | 8/1991 | Tsuchida et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,085,632 A | 2/1992 | Ikada et al. |
| 5,106,368 A | 4/1992 | Uldall et al. |
| 5,135,599 A | 8/1992 | Martin et al. |
| 5,158,592 A | 10/1992 | Martin et al. |
| 5,167,623 A | 12/1992 | Cianci et al. |
| 5,171,227 A | 12/1992 | Twardowski et al. |
| 5,188,593 A | 2/1993 | Martin |
| 5,190,520 A | 3/1993 | Fenton, Jr. et al. |
| 5,195,962 A | 3/1993 | Martin et al. |
| 5,197,951 A | 3/1993 | Mahurkar |
| 5,209,723 A | 5/1993 | Twardowski et al. |
| 5,219,335 A | 6/1993 | Willard et al. |
| 5,221,255 A | 6/1993 | Mahurkar et al. |
| 5,221,256 A * | 6/1993 | Mahurkar ............... 604/43 |
| 5,273,527 A | 12/1993 | Schatz et al. |
| 5,281,134 A | 1/1994 | Schultz |
| 5,282,788 A | 2/1994 | Wilk et al. |
| 5,290,282 A | 3/1994 | Casscells |
| 5,308,338 A | 5/1994 | Helfrich |
| 5,318,518 A | 6/1994 | Plechinger et al. |
| 5,336,165 A | 8/1994 | Twardowski |
| 5,346,471 A | 9/1994 | Raulerson |
| 5,348,536 A | 9/1994 | Young et al. |
| 5,360,397 A | 11/1994 | Pinchuk |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,395,316 A | 3/1995 | Martin |
| 5,403,291 A | 4/1995 | Abrahamson |
| 5,405,341 A | 4/1995 | Martin |
| 5,419,777 A | 5/1995 | Hofling |
| 5,419,216 A | 9/1995 | Quinn |
| 5,451,206 A | 9/1995 | Young |
| 5,464,398 A | 11/1995 | Haindl |
| 5,472,417 A | 12/1995 | Martin et al. |
| 5,480,380 A | 1/1996 | Martin |
| 5,486,159 A | 1/1996 | Mahurkar |
| 5,489,278 A | 2/1996 | Abrahamson |
| 5,509,897 A | 4/1996 | Twardowski et al. |
| 5,536,234 A | 7/1996 | Newman |
| 5,549,541 A | 8/1996 | Muller |
| 5,554,136 A | 9/1996 | Luther |
| 5,556,390 A | 9/1996 | Hicks |
| 5,562,640 A | 10/1996 | McCabe et al. |
| 5,569,182 A | 10/1996 | Twardowski et al. |
| 5,571,093 A | 11/1996 | Cruz et al. |
| 5,607,440 A | 3/1997 | Danks et al. |
| D381,420 S | 7/1997 | Musgrave et al. |
| D384,411 S | 9/1997 | Musgrave et al. |
| D384,741 S | 10/1997 | Musgrave et al. |
| 5,683,640 A | 11/1997 | Miller et al. |
| 5,685,867 A | 11/1997 | Twardowski et al. |
| 5,702,365 A | 12/1997 | King |
| 5,707,351 A | 1/1998 | Dorsey, III |
| 5,718,678 A | 2/1998 | Fleming, III |
| 5,725,495 A | 3/1998 | Strukel et al. |
| 5,776,092 A | 7/1998 | Farin et al. |
| 5,776,096 A | 7/1998 | Fields |
| 5,782,797 A | 7/1998 | Schweich, Jr. et al. |
| 5,785,678 A | 7/1998 | Griep et al. |
| 5,788,680 A | 8/1998 | Linder |
| 5,788,681 A | 8/1998 | Weaver et al. |
| 5,797,869 A | 8/1998 | Martin et al. |
| 5,801,012 A | 9/1998 | Soff et al. |
| 5,807,311 A | 9/1998 | Patestrant |
| 5,807,329 A | 9/1998 | Gelman |
| 5,810,789 A | 9/1998 | Powers et al. |
| 5,830,184 A | 11/1998 | Basta |
| 5,830,196 A | 11/1998 | Hicks |
| 5,858,009 A | 1/1999 | Jonkman |
| 5,868,717 A | 2/1999 | Prost |
| 5,902,476 A | 5/1999 | Twardowski |
| 5,947,953 A | 9/1999 | Ash et al. |
| 5,961,485 A | 10/1999 | Martin |
| 5,961,486 A | 10/1999 | Twardowski et al. |
| 5,976,103 A | 11/1999 | Martin |
| 5,989,206 A | 11/1999 | Prosl et al. |
| 5,989,213 A | 11/1999 | Maginot |
| 5,993,437 A | 11/1999 | Raoz |
| 6,001,079 A | 12/1999 | Pourchez |
| 6,004,310 A | 12/1999 | Bardsley et al. |
| 6,063,099 A | 5/2000 | Danks et al. |
| 6,086,565 A | 7/2000 | Ouchi |
| 6,099,519 A | 8/2000 | Olsen et al. |
| 6,123,725 A | 9/2000 | Aboul-Hosn |
| 6,126,631 A | 10/2000 | Loggie |
| 6,132,616 A | 10/2000 | Twardowski et al. |
| 6,146,354 A | 11/2000 | Beil |
| 6,146,536 A | 11/2000 | Twardowski |
| 6,152,910 A | 11/2000 | Agro et al. |
| 6,156,018 A | 12/2000 | Maginot |
| 6,190,349 B1 | 2/2001 | Ash et al. |
| 6,190,357 B1 | 2/2001 | Ferrari et al. |
| 6,190,371 B1 | 2/2001 | Maginot et al. |
| 6,206,849 B1 | 3/2001 | Martin et al. |
| 6,273,875 B1 | 8/2001 | Siman et al. |
| 6,280,423 B1 | 8/2001 | Davey et al. |
| 6,293,927 B1 | 9/2001 | McGuckin, Jr. |
| 6,299,444 B1 | 10/2001 | Cohen |
| 6,342,120 B1 | 1/2002 | Basta |
| 6,346,090 B1 | 2/2002 | Liska et al. |
| 6,394,141 B2 | 5/2002 | Wages et al. |
| 6,409,700 B1 | 6/2002 | Siegel, Jr. et al. |
| 6,423,050 B1 | 7/2002 | Twardowski |
| 6,428,502 B1 | 8/2002 | Lang |
| 6,447,488 B2 | 9/2002 | Estabrook et al. |
| 6,461,321 B1 | 10/2002 | Quinn |
| 6,475,207 B1 | 11/2002 | Maginot et al. |
| 6,482,169 B1 | 11/2002 | Kuhle |

(56) References Cited

U.S. PATENT DOCUMENTS

| | | |
|---|---|---|
| 6,506,182 B2 | 1/2003 | Estabrook et al. |
| 6,517,529 B1 | 2/2003 | Quinn |
| 6,576,609 B1 | 6/2003 | Soff et al. |
| 6,579,261 B1 | 6/2003 | Kawamura |
| 6,585,705 B1 | 7/2003 | Maginot et al. |
| 6,592,542 B2 | 7/2003 | Childers et al. |
| 6,592,558 B2 | 7/2003 | Quah |
| 6,592,565 B2 | 7/2003 | Twardowski |
| 6,595,966 B2 | 7/2003 | Davey et al. |
| 6,620,118 B1 | 9/2003 | Prosl et al. |
| 6,638,242 B2 | 10/2003 | Wilson et al. |
| 6,692,473 B2 | 2/2004 | St. Cyr et al. |
| 6,695,832 B2 | 2/2004 | Schon et al. |
| 6,719,749 B1 | 4/2004 | Schweikert et al. |
| 6,723,084 B1 | 4/2004 | Maginot et al. |
| 6,730,096 B2 | 5/2004 | Basta |
| 6,743,218 B2 | 6/2004 | Maginot et al. |
| 6,749,580 B2 | 6/2004 | Work et al. |
| 6,758,836 B2 | 7/2004 | Zawacki |
| 6,786,884 B1 | 9/2004 | DeCant, Jr. et al. |
| 6,808,510 B1 | 10/2004 | DiFiore |
| 6,814,718 B2 | 11/2004 | McGuckin, Jr. et al. |
| 6,858,019 B2 | 2/2005 | McGuckin, Jr. et al. |
| 6,872,198 B1 | 3/2005 | Wilson et al. |
| 6,886,752 B2 | 5/2005 | Murayama et al. |
| 6,911,014 B2 | 6/2005 | Wentling et al. |
| 6,921,396 B1 | 7/2005 | Wilson et al. |
| 6,942,635 B2 | 9/2005 | Rosenblatt et al. |
| 6,942,653 B2 | 9/2005 | Quinn |
| 6,968,886 B2 | 11/2005 | Appling |
| 6,969,381 B2 | 11/2005 | Voorhees |
| 6,976,973 B1 | 12/2005 | Ruddell et al. |
| 6,991,625 B1 | 1/2006 | Gately et al. |
| 7,008,395 B1 | 3/2006 | Loggie |
| 7,008,412 B2 | 3/2006 | Maginot |
| 7,011,645 B2 | 3/2006 | McGuckin, Jr. et al. |
| 7,013,928 B2 | 3/2006 | Navis |
| 7,048,680 B2 | 5/2006 | Viole et al. |
| 7,066,914 B2 | 6/2006 | Andersen |
| 7,077,829 B2 | 7/2006 | McGuckin, Jr. et al. |
| 7,141,035 B2 | 11/2006 | Haggstrom |
| 7,223,263 B1 | 5/2007 | Seno |
| 7,322,953 B2 * | 1/2008 | Redinger ............... 604/43 |
| 7,569,029 B2 | 8/2009 | Clark |
| 2002/0121282 A1 | 9/2002 | McGuckin |
| 2002/0156430 A1 | 10/2002 | Haarala et al. |
| 2002/0165492 A1 | 11/2002 | Davey et al. |
| 2003/0032918 A1 | 2/2003 | Quinn |
| 2003/0093028 A1 | 5/2003 | McGuckin, Jr. et al. |
| 2003/0191425 A1 | 10/2003 | Rosenblatt |
| 2004/0006318 A1 * | 1/2004 | Periakaruppan et al. .... 604/264 |
| 2004/0167463 A1 | 8/2004 | Zawacki et al. |
| 2004/0249337 A1 | 12/2004 | DiFiore |
| 2005/0033222 A1 | 2/2005 | Haggstrom et al. |
| 2005/0033264 A1 | 2/2005 | Redinger |
| 2005/0085765 A1 | 4/2005 | Voorhees |
| 2005/0090776 A1 | 4/2005 | McGuckin, Jr. et al. |
| 2005/0177094 A1 | 8/2005 | Igarashi et al. |
| 2005/0215978 A1 | 9/2005 | Ash |
| 2005/0228339 A1 | 10/2005 | Clark |
| 2005/0267400 A1 | 12/2005 | Haarala et al. |
| 2005/0288623 A1 | 12/2005 | Hjalmarsson |
| 2006/0004316 A1 * | 1/2006 | Difiore et al. ............ 604/6.16 |
| 2006/0004325 A1 | 1/2006 | Hamatake et al. |
| 2007/0100298 A1 | 5/2007 | Appling |
| 2008/0082080 A1 * | 4/2008 | Braga ..................... 604/523 |
| 2009/0112153 A1 | 4/2009 | Gregersen et al. |
| 2009/0118661 A1 | 5/2009 | Moehle et al. |
| 2009/0192435 A1 | 7/2009 | Gregersen |
| 2010/0069818 A1 | 3/2010 | Smouse |
| 2010/0076404 A1 | 3/2010 | Ring |
| 2010/0081986 A1 | 4/2010 | Matson et al. |
| 2011/0130745 A1 | 6/2011 | Shevgoor et al. |

FOREIGN PATENT DOCUMENTS

| | | |
|---|---|---|
| EP | 0107810 | 5/1984 |
| EP | 0 299 622 | 1/1989 |
| EP | 0 341 721 | 11/1989 |
| EP | 0 554 722 | 8/1993 |
| EP | 0 623 356 | 11/1994 |
| EP | 0 322 225 | 2/1995 |
| EP | 0 713 406 | 3/1998 |
| EP | 0 570 530 | 8/1999 |
| EP | 0 555 780 | 9/1999 |
| EP | 1 144 039 | 12/2005 |
| EP | 1 905 476 A2 | 4/2008 |
| EP | 2119468 A1 | 11/2009 |
| EP | 2168625 A1 | 3/2010 |
| FR | 2 326 941 | 10/1976 |
| GB | 2028136 | 3/1980 |
| JP | 08103492 | 4/1996 |
| JP | 8308933 | 11/1996 |
| JP | 2004-174130 A | 6/2004 |
| WO | WO 92/14500 | 9/1992 |
| WO | WO 95/04567 | 2/1995 |
| WO | WO 95/10317 | 4/1995 |
| WO | WO 97/37699 | 10/1997 |
| WO | WO 98/41277 | 9/1998 |
| WO | WO 99/38550 | 8/1999 |
| WO | WO 99/65557 | 12/1999 |
| WO | WO 01/91845 | 12/2001 |
| WO | WO 02/13899 | 2/2002 |
| WO | WO 02/018004 | 3/2002 |
| WO | WO 03/033049 | 4/2003 |
| WO | WO 03/066148 | 8/2003 |
| WO | WO 2004/093956 | 11/2004 |
| WO | WO 2005/023336 | 3/2005 |
| WO | WO 2005/077449 | 8/2005 |
| WO | WO 2005/084741 | 9/2005 |
| WO | WO 2006/014339 | 2/2006 |
| WO | 2007/111874 A2 | 10/2007 |
| WO | WO2008/155145 A1 | 12/2008 |

OTHER PUBLICATIONS

Bard Access Systems Power-Trialysis Short-Term Dialysis Catheter—Short-Term Triple Lumen Dialysis Catheter, Enhanced Acute Dialysis Care.

European Search Report from EP 12 17 0080 dated Aug. 16, 2012.

Office Action issued in corresponding Chinese Application No. 201010624264.6 dated Jul. 25, 2013.

First Office Action issued in Chinese Appl. No. 201210059962.5 dated Apr. 26, 2013.

Official Action issued in Japanese Appl. No. 2012-214681 dated Aug. 28, 2013.

Office Action issued in Japanese Application No. 2012-212145 dated Aug. 28, 2013.

Examiner's Report issued in Australian Appl. No. 2012230094 dated Sep. 12, 2013.

Notification of Reexamination, and translation thereof, from counterpart Chinese Patent Application No. 201010624264.6, dated Oct. 13, 2014, 19 pp.

Examination Report from counterpart European Patent Application No. 10184012.2, dated Mar. 30, 2015, 4 pp.

Examination Report from counterpart European Application No. 12170080.1, dated Dec. 17, 2015, 3 pp.

Examination Report from counterpart European Application No. 10184012.2, dated Oct. 27, 2017, 5 pp.

* cited by examiner

MEDICAL CATHETER HAVING A DESIGN PROVIDING LOW RECIRCULATION AND REVERSIBILITY

CROSS-REFERENCE TO RELATED APPLICATIONS

This application claims the benefit of, and priority to, U.S. Provisional Patent Application Ser. No. 61/247,101, filed Sep. 30, 2009, and U.S. Provisional Patent Application Ser. No. 61/289,073, filed Dec. 22, 2009, the entire contents of each being incorporated by reference herein.

BACKGROUND

1. Technical Field

The present disclosure relates to a catheter assembly, and in particular, to a hemodialysis catheter assembly adapted to facilitate bidirectional fluid flow.

2. Description of the Related Art

Catheters are flexible medical instruments for use in the introduction and withdrawal of fluids to and from body cavities, ducts, and vessels. Catheters have particular application in hemodialysis procedures, in which blood is withdrawn from a blood vessel for treatment and subsequently returned to the blood vessel for circulation through a patient's body.

Many hemodialysis catheters include multiple lumens, e.g., dual or triple-lumen catheters, with one lumen being dedicated to the withdrawal of fluid from a vessel via communication in one direction, and at least one other lumen being dedicated to the return of fluid to the vessel via communication in another direction. Generally, the lumen through which fluid is withdrawn is referred to as the "arterial" lumen, and the lumen through which fluid is returned is referred to as the "venous" lumen. Fluid enters the arterial lumen and exits the venous lumen through corresponding openings in the catheter wall. During an exemplary hemodialysis procedure, after placement of a multiple lumen catheter, blood is withdrawn from the patient through the arterial lumen of the catheter, and is directed to a hemodialysis unit for dialysis, or purification, to remove waste and toxins. The dialyzed blood is then returned to the patient through the venous lumen of the catheter.

Known hemodialysis catheters incorporate various catheter tip designs. For example, a catheter may include a design with staggered venous and arterial lumens, and thus, staggered venous and arterial openings. The staggered openings ensure blood returning to the patient will be expelled from the venous lumen downstream of the arterial opening. However, poor flow performance often occurs due to occlusion in the arterial lumen of the catheter resulting from, e.g., positional occlusion, or the formation of a fibrin sheath or thrombus.

Current measures taken to resolve flow occlusion include repositioning the patient, flushing the lumens of the catheter, and reversing the blood lines of the catheter to the hemodialysis unit. However, these measures create a situation wherein cleaned blood is expelled upstream relative to the catheter inlet, which may undesirably increase the potential for clean blood being drawn back into the catheter. This "recirculation" of the blood results in inefficient dialysis by increasing treatment time to reach prescribed blood cleanliness levels.

Several factors pertaining to the venous and arterial openings in the wall of a catheter have been found to impact the likelihood of occlusion and recirculation during a hemodialysis procedure. These factors include, for example, the circumferential and axial distances between the openings, and the perimeter and circumferential heights thereof. Known catheter tip designs, however, are deficient in the optimization of one or more of these factors. For example, U.S. Pat. Nos. 5,403,291 and 5,489,278, each to Abrahamson, disclose a catheter assembly including a body portion defining longitudinally spaced intake and return lumens in respective fluid communication with a side opening formed in a wall of the body portion and an opening formed at the distal tip. The side opening is defined by two pairs of generally parallel wall portions, and the opening at the distal tip is substantially circular in configuration.

Additional examples of known catheter tip designs are disclosed in U.S. Pat. Nos. 5,685,867 and 5,961,486, each to Twardowski, et al, which disclose a catheter including internal venous and arterial lumens. The venous and arterial lumens are in communication with corresponding openings positioned at the distal end of the catheter that are spaced longitudinally from each other.

Given the desirability of reducing the likelihood of occlusion and limiting recirculation, a catheter tip design including structure that optimizes one or more of the factors identified above would be advantageous.

SUMMARY

In one embodiment of the present disclosure, a medical catheter is disclosed that includes an elongate catheter member defining a longitudinal axis and having a proximal end, a distal end, an outer wall, and first and second internal lumens. Alternatively, the catheter may include a third internal lumen extending therethrough, wherein the first, second, and third internal lumens are separated by at least two septums extending inwardly from the outer wall.

The outer wall of the catheter member defines a first opening in fluid communication with the first internal lumen to facilitate the establishment of a first flow stream, and a second opening in fluid communication with the second internal lumen to facilitate the establishment of a second flow stream. The configurations, dimensions, and positioning of the first and second openings maximize separation of the first flow stream from the second flow stream in order to reduce the likelihood of recirculation between the first and second internal lumens. To this end, in one embodiment, it is envisioned that each of the first and second openings may include proximal and distal tapered portions that are connected by an intermediate portion having a constant transverse dimension. The proximal tapered portions of the first and second openings included in the outer wall of the catheter member may include a transverse dimension that increases in a distal direction. Additionally, or alternatively, the distal tapered portions of the first and second openings may include a transverse dimension that decreases in a distal direction.

The first opening is defined by a first continuous wall, and the second opening is defined by a second continuous wall, where each of the first and second continuous walls includes first and second axial wall portions extending along an axis parallel to the longitudinal axis, and first and second transverse wall portions connecting the first and second axial wall portions. In one embodiment of the disclosed catheter, the first axial wall portions define a first length, and the second axial wall portions define a second, greater length. It is envisioned that at least one of the first and second transverse wall portions may include an arcuate configuration, e.g., curving towards the second axial wall portion. For example, each of the first and second transverse wall portions may include an arcuate configuration.

The first axial wall portions define a first distance therebetween measured along a circumference of the catheter member, and the second axial wall portions define a second distance therebetween measured along a circumference of the catheter member. The first distance and the second distance may be equal to thereby maximize separation of the first and second openings.

In one particular embodiment of the disclosed catheter, the first and second openings included in the outer wall are identical in configuration and dimensions.

In another aspect of the present disclosure, a medical catheter is disclosed that includes an elongate catheter extending along a longitudinal axis and having a proximal end, a distal end, an outer wall, and first and second internal lumens. The outer wall defines a first opening in fluid communication with the first internal lumen to facilitate the establishment of a first flow stream, and a second opening in fluid communication with the second internal lumen to facilitate the establishment of a second flow stream.

The first opening is defined by a first continuous wall having first and second transversely spaced axial wall portions, and the second opening is defined by a second continuous wall having first and second transversely spaced axial wall portions, wherein the first axial wall portions and the second axial wall portions define an equivalent distance therebetween measured along a circumference of the catheter to maximize separation of the first and second openings. It is envisioned that the first axial wall portions may define a first length, and that the second axial wall portions may define a second, greater length.

The first and second axial wall portions of the first wall are connected by a pair of first transverse wall portions, and the first and second axial wall portions of the second wall are connected by a pair of second transverse wall portions.

It is envisioned that the first and second openings may each include at least one transverse wall portion having an arcuate configuration.

It is also envisioned that the first and second openings may each include proximal and distal tapered portions that are connected by an intermediate portion having a constant transverse dimension. For example, the proximal tapered portions of the first and second openings may include a transverse dimension that increases in a distal direction. Additionally, or alternatively, the distal tapered portions of the first and second openings may include a transverse dimension that decreases in a distal direction.

In still another aspect of the present disclosure, a method of manufacturing a medical catheter is disclosed to reduce recirculation of fluid between internal lumens of the catheter during a medical procedure. The method includes the steps of (i) providing an elongate member extending along a longitudinal axis, the elongate member including an outer wall and defining first and second internal lumens extending through the elongate member; (ii) forming a first opening in the outer wall of the elongate member in communication with the first internal lumen to facilitate establishment of a first flow stream through the catheter, wherein the first opening includes proximal and distal tapered portions; and (iii) forming a second opening in the outer wall of the elongate member in communication with the second internal lumen to facilitate establishment of a second flow stream through the catheter, wherein the second opening includes proximal and distal tapered portions, the first and second openings being configured, dimensioned, and positioned to maximize separation of the proximal portion of the first opening from the distal portion of the second opening to maximize separation of the first and second flow streams.

It is envisioned that the step of forming first and second openings in the outer wall of the elongate member may include forming first and second openings each including an intermediate portion with a constant transverse dimension that connects the proximal and distal tapered portions. The proximal tapered portions of the first and second openings may include a transverse dimension that increases in a distal direction. Additionally, or alternatively, the distal tapered portions of the first and second openings may include a transverse dimension that decreases in a distal direction.

It is further envisioned that the steps of forming first and second openings in the outer wall of the elongate member may include forming a first opening defined by a first continuous wall, and a second opening defined by a second continuous wall. In one embodiment of the disclosed method, it is envisioned that the first and second walls may each be defined by first and second axial wall portions extending along an axis parallel to the longitudinal axis of the elongate member, and that the first and second transverse wall portions may connect the first and second axial wall portions. For example, it is envisioned that the first axial wall portions may define a first length, whereas the second axial wall portions may define a second, greater length.

It is further envisioned that the steps of forming first and second openings in the outer wall of the elongate member may include forming first and second openings, wherein either or both of the first and second transverse wall portions includes an arcuate configuration, e.g., an arcuate configuration that curves towards the second axial wall portions.

In one particular method of manufacture, the steps of forming first and second openings in the outer wall of the elongate member may include forming first and second openings that are identical in configuration and dimensions.

In an additional aspect of the present disclosure, a medical catheter assembly is disclosed that includes an elongate catheter member extending along a longitudinal axis, and having a proximal end, a distal end, and an outer wall.

The elongate catheter member defines a first internal lumen and a second internal lumen. The outer wall includes a first opening in fluid communication with the first internal lumen to facilitate establishment of a first flow stream, and a second opening in fluid communication with the second internal lumen to facilitate establishment of a second flow stream. The first and second openings are positioned in diametrical opposition to thereby maximize separation of the first and second openings, whereby separation of the first flow stream from the second flow stream is maximized to reduce the likelihood of recirculation between the first and second internal lumens.

The first opening is defined by a first continuous wall having first and second transversely spaced wall portions, wherein at least one of the first and second wall portions of the first wall has an arcuate configuration, and the second opening is defined by a second continuous wall having first and second transversely spaced wall portions, wherein at least one of the first and second wall portions of the second wall has an arcuate configuration.

In one embodiment of the disclosed catheter assembly, it is envisioned that both the first and second wall portions of the first wall may be arcuate in configuration, and that both the first and second wall portions of the second wall may be arcuate in configuration.

In another aspect of the present disclosure, a medical catheter assembly is disclosed that includes an elongate catheter member defining first and second internal lumens extending therethrough.

The elongate catheter member includes an outer wall having a first opening defined by a first continuous wall, wherein the first opening is in fluid communication with the first internal lumen to facilitate establishment of a first flow stream, and a second opening defined by a second continuous wall, wherein the second opening is in fluid communication with the second internal lumen to facilitate establishment of a second flow stream.

The first and second openings each include proximal and distal tapered portions, whereby separation of the first flow stream from the second flow stream is maximized to reduce the likelihood of recirculation between the first and second internal lumens.

The proximal and distal tapered portions of the first opening are connected by a first intermediate portion, and the proximal and distal tapered portions of the second opening are connected by a second intermediate portion.

The first intermediate portion is defined by first and second wall portions of the first wall, and the second intermediate portion is defined by first and second wall portions of the second wall. At least one of the first and second wall portions defining the first intermediate portion is arcuate in configuration, and at least one of the first and second wall portions defining the second intermediate portion is arcuate in configuration.

In one embodiment of the disclosed catheter assembly, it is envisioned that each of the first wall portion and the second wall portion defining the first intermediate portion may be arcuate in configuration, and that each of the first wall portion and the second wall portion defining the second intermediate portion may be arcuate in configuration.

BRIEF DESCRIPTION OF THE DRAWINGS

Various embodiments of the present disclosure will be described herein with references to the accompanying drawings, wherein.

DETAILED DESCRIPTION OF THE EMBODIMENTS

Various exemplary embodiments of the present disclosure are discussed herein below in terms of medical catheters for the administration of fluids, i.e., withdrawal and introduction, relative to the body of a subject and, more particularly, in terms of a hemodialysis catheter. However, it is envisioned that the principles of the present disclosure are equally applicable to a range of catheter applications including surgical, diagnostic and related treatments of diseases and body ailments of a subject. It is further envisioned that the principles relating to the presently disclosed catheter may be equally applicable to a variety of catheter related procedures, such as, for example, hemodialysis, cardiac, abdominal, urinary, intestinal, including both chronic and acute applications. Moreover, the catheter can be used for administration of fluids such as, for example, medication, saline, bodily fluids, blood and urine.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human patient or other animal, and the term "clinician" should be understood as referring to a doctor, nurse or other care provider and may include support personnel.

Figure 1:
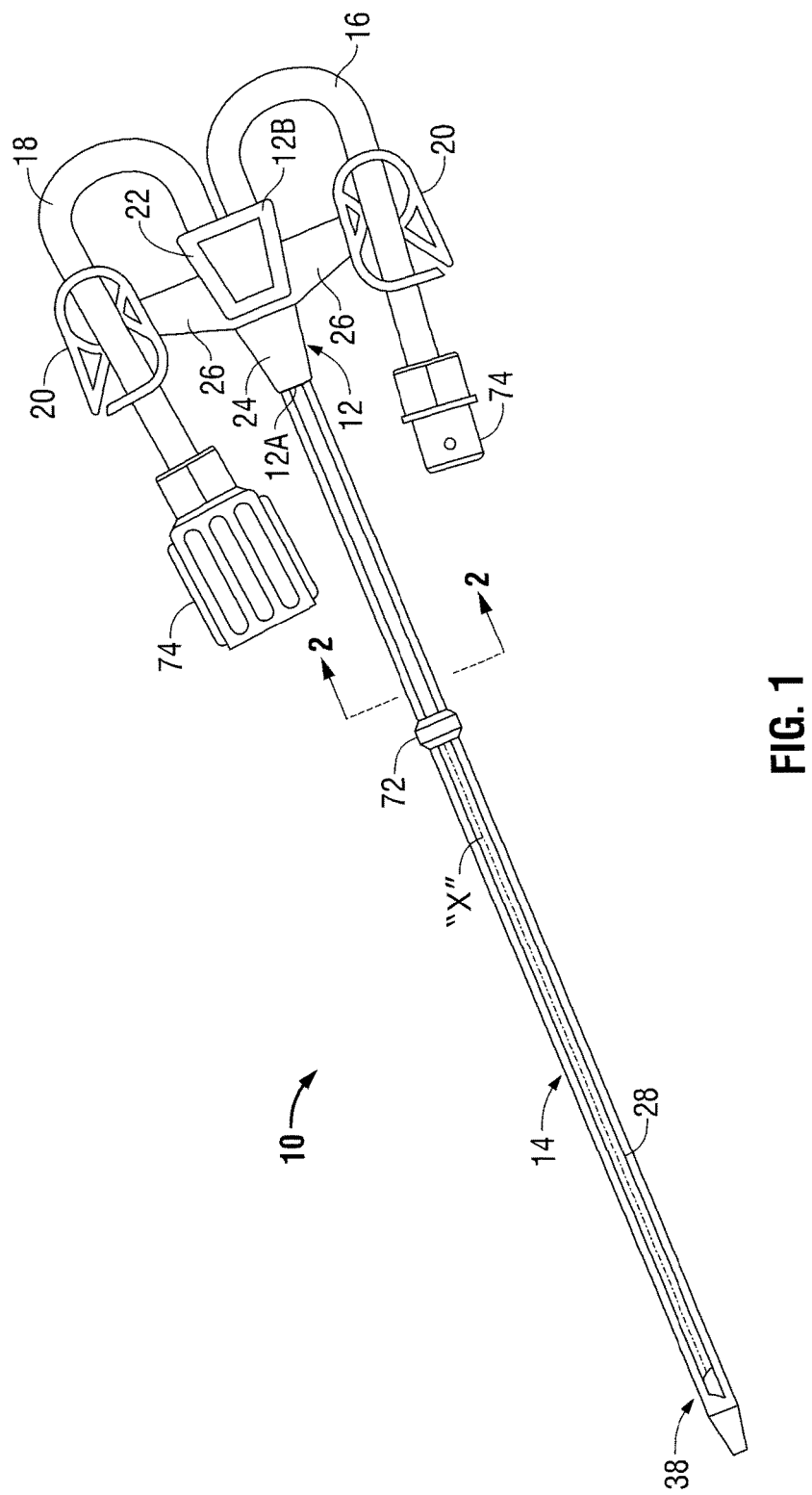
FIG. 1 is a perspective view of one embodiment of a catheter assembly in accordance with the principles of the present disclosure that includes a catheter hub, an elongated catheter member extending distally from the catheter hub, and first and second extension tubes extending proximally from the catheter hub.

Referring now to the drawings, wherein like components are designated by like reference numerals throughout the several views, FIG. 1 illustrates a hemodialysis catheter assembly 10 in accordance with the principles of the present disclosure. The catheter assembly 10 includes a catheter hub or housing 12 having respective distal and proximal ends 12A, 12B, an elongated catheter member 14 that extends distally from the catheter hub 12, and first and second extension tubes 16, 18 that extend proximally from the catheter hub 12. The catheter assembly 10 may be provided with the hub 12 integrally formed with the catheter member 14. Alternatively, the hub 12 may be configured for attachment to the catheter member 14 after catheter placement into a patient by the clinician. The catheter assembly 10 further includes a pair of clamps 20 that are positionable about the extension tubes 16, 18. Each clamp 20 is movable from an open position to a substantially closed position to compress a corresponding extension tube 16, 18, and thereby inhibit fluid flow through the extension tubes 16, 18.

The catheter hub 12 is advantageously dimensioned for engagement by the clinician, and includes a proximal (trailing) housing section 22 that is positioned adjacent the extension tubes 16, 18, and a distal (leading) housing section 24 that is positioned adjacent the catheter member 14. The proximal housing section 22 is adapted to respectively receive the first and second extension tubes 16, 18 in secured relation. For example, the extension tubes 16, 18 may be secured within respective extension conduits (not shown) of the catheter hub 12 through the employ of an interference or frictional fit, cements, adhesives, or in any other suitable manner. The distal housing section 24 of the catheter hub 12 defines a central opening (not shown) that is configured and dimensioned to receive the catheter member 14 in secured relation, e.g., through the employ of an interference or frictional fit, cements, adhesives, or in any other suitable manner.

In the embodiment of the catheter assembly 10 illustrated in FIG. 1, the catheter hub 12 further includes a pair of opposed wings 26 that depend outwardly from the catheter hub 12. The wings 26 serve as a surface about which one or more sutures (not shown) may be secured to fix the catheter hub 12 relative to the patient. Alternatively, the wings 26 or the catheter hub 12 may include an annular groove (not shown) in an outer surface thereof that is configured and dimensioned to receive a suture(s), in which case, the suture(s) may be positioned within the annular groove, and subsequently secured to the patient.

Figure 2:
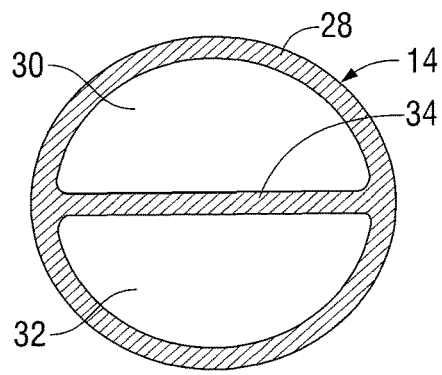
FIG. 2 is a cross-sectional view taken along line 2-2 in FIG. 1 illustrating a dual lumen configuration for the catheter member.

Referring now to FIG. 2 as well, the elongated catheter member 14 will be discussed. The catheter member 14 may be formed from either a substantially flexible material, or a material that is more rigid in construction, dependent upon the particular application in which the catheter member 14 will be employed, e.g., a chronic or an acute application. For example, the catheter member 14 may be formed, either partially or wholly, from polymerics or metals, such as titanium and stainless steel, medical grade polyurethane, silicone, or the like. One skilled in the art, however, will realize that other suitable materials, in accordance with the present disclosure, would also be appropriate. The catheter body 14 may be formed through any suitable method of manufacture, including but not limited to conventional injection molding or extrusion processes.

The catheter member 14 may include a pre-curved configuration in a normal state thereof such that the catheter member 14 is normally biased towards an arcuate configuration in the absence of any external forces in order to conform to the configuration of the target tissue, e.g., the body cavity or vessel into which the catheter member 14 is inserted. Alternatively, the catheter member 14 may be devoid of any normally arcuate configuration.

Figure 2A:
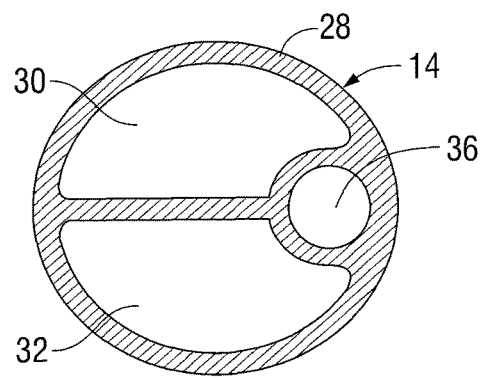
FIG. 2A is a cross-sectional view also taken along line 2-2 in FIG. 1 illustrating an alternative configuration for the catheter member.

Referring to FIGS. 1-2A, the catheter member 14 includes an outer wall 28, and defines a longitudinal axis "X." It is envisioned that the outer wall 28 of catheter member 14 may include reinforcing material to increase the stability and rigidity thereof, if necessary or desired. As shown in FIG. 2, in one embodiment of the disclosure, the catheter member 14 may assume a dual lumen configuration including respective first and second internal lumens 30, 32 that are separated by a septum wall 34, which may or may not extend the length the catheter member 14. In this embodiment, the respective first and second longitudinal lumens 30, 32 are each configured and dimensioned for fluid communication, e.g., blood, and may include any cross-sectional configuration suitable for this intended purpose, including but not limited to oblong, kidney-shaped, D-shaped, circular, pie shaped, or the like. While it is envisioned that either lumen 30, 32 may function as the intake (arterial) lumen or the return (venous) lumen, throughout the following discussion, the lumen 30 will be referred to as the venous lumen and the lumen 32 will be referred to as the arterial lumen. Although illustrated as side-by-side in orientation in FIG. 2, the lumens 30, 32 may also be positioned in coaxial relation.

As shown in FIG. 2A, in an alternative embodiment, the catheter member 14 may include a guidewire channel 36 that is configured and dimensioned for the reception and passage of a guidewire (not shown) utilized to facilitate entry of the catheter member 14 into the target tissue site, e.g., a vascular organ, as is known and conventional in the art. It is also envisioned that the guidewire channel 36 may be employed in the infusion of a fluid, such as a medicament or the like. Alternatively, one of longitudinal lumens 30, 32 extending through the catheter member 14 may serve as a guidewire channel, in addition to functioning as either a venous or arterial lumen.

Figure 2B:
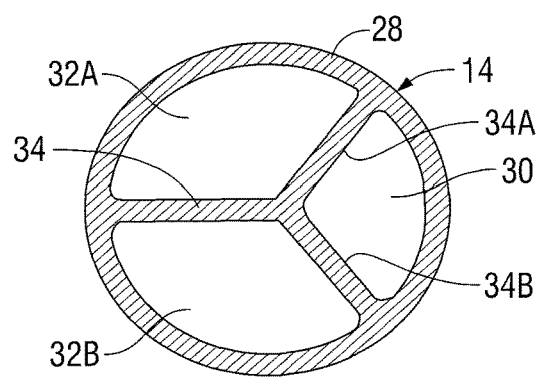
FIG. 2B is a cross-sectional view also taken along line 2-2 in FIG. 1 illustrating a triple lumen configuration for the catheter member.
Figure 3:
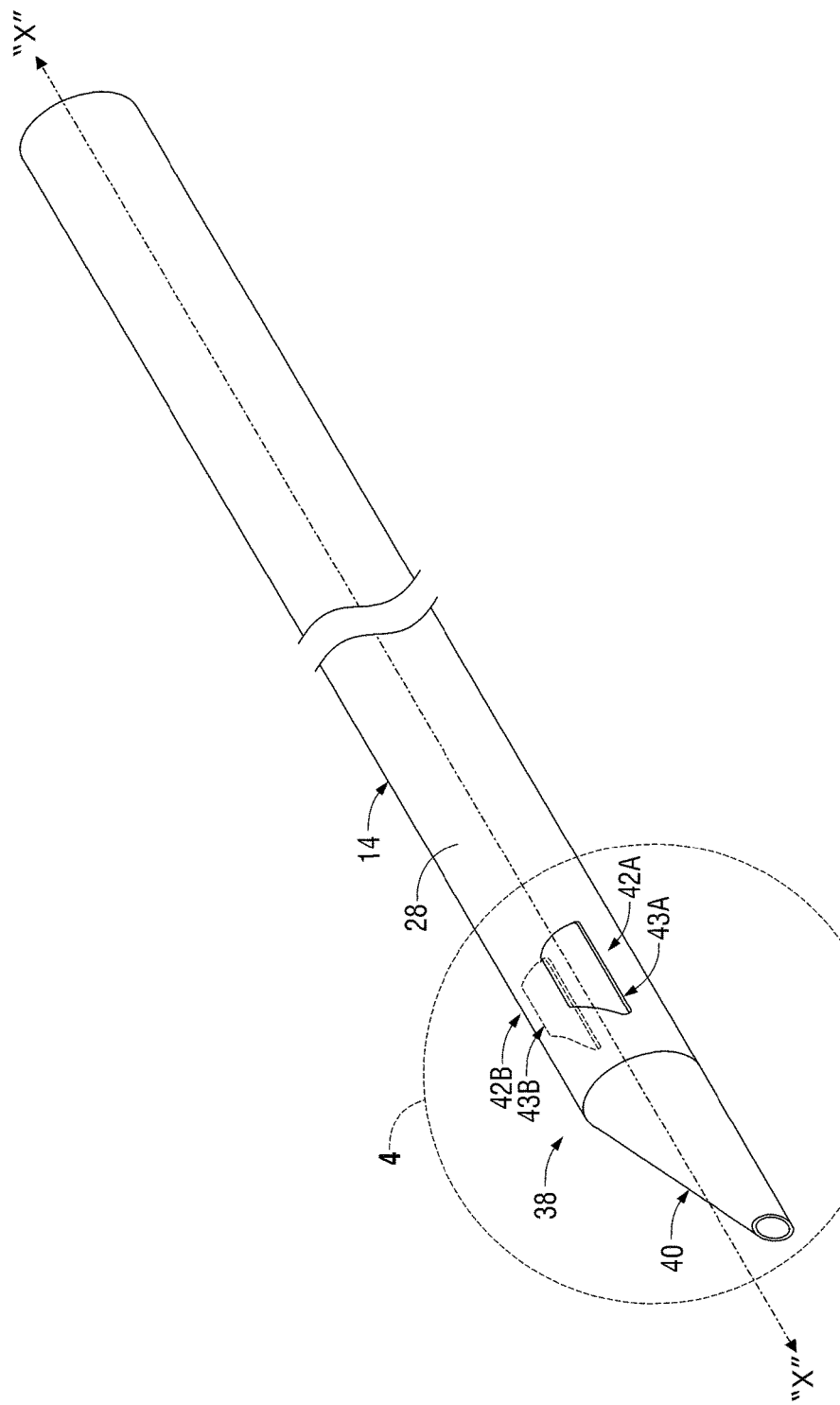
FIG. 3 is a side, perspective view of a distal portion of the catheter member.

Although the catheter member 14 is illustrated in FIGS. 2 and 2A with a dual lumen configuration, it is also contemplated herein that the catheter member 14 may include any suitable number of additional internal lumens. For example, the catheter member 14 may assume a triple lumen configuration including three internal lumens 30, 32A, 32B separated by septum walls 34, 34A, 34B, as illustrated in FIG. 2B.

Referring now to FIGS. 3-7, the catheter member 14 includes a leading (distal) end 38 with a catheter tip member 40 integrally formed therewith, or mounted thereto, that is advantageously configured and dimensioned to facilitate initial insertion into body tissue. Details regarding the structure and function of the catheter tip member 40 may be obtained through reference to U.S. Patent Application Publication No. 20080082080, filed on Sep. 29, 2006, the entire contents of which are incorporated by reference herein. The leading end 38 of the catheter member 14 further includes respective first and second openings 42A, 42B defined by the outer wall 28. The first opening 42A is in fluid communication with the first internal lumen 30 (FIG. 2) extending through the catheter member 14, thus functioning as a venous opening, and the second opening 42B is in fluid communication with the second internal lumen 32 (FIG. 2) extending through the catheter member 14, thus functioning as an arterial opening. It is envisioned that respective venous and arterial openings 42A, 42B may be formed in any suitable method during manufacture, including but not being limited to laser machining. In the embodiment of the catheter member 14 illustrated in FIGS. 3-7, the respective venous and arterial openings 42A, 42B are positioned at the same axial location along the longitudinal axis "X" of the catheter member 14. However, in alternative embodiments of the present disclosure, the venous opening 42A may be spaced from the arterial opening 42B along the longitudinal axis "X" of the catheter member 14, e.g., to adjust the communication of fluid into and out of the catheter member 14. For example, it is envisioned that the respective venous and arterial openings 42A, 42B may be positioned within 5 mm of each other along the longitudinal axis "X," although increased axial spacing between the respective venous and arterial openings 42A, 42B is not beyond the scope of the present disclosure.

Figure 6:
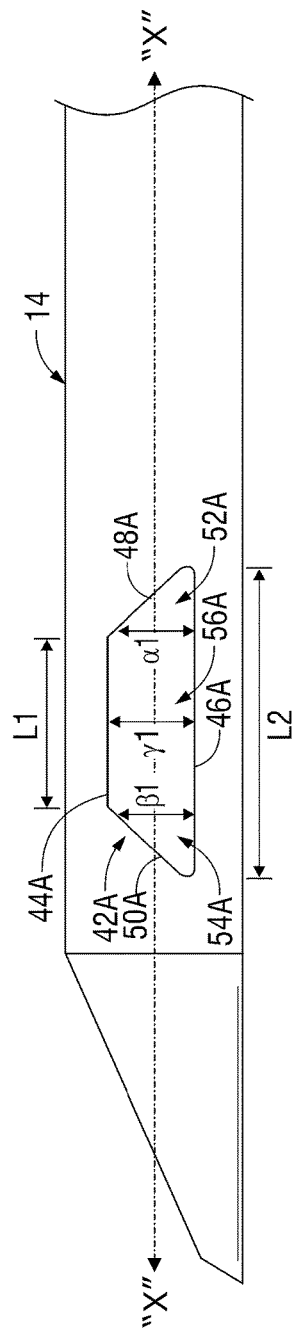
FIG. 6 is a side, plan view of a distal portion of the catheter member illustrating a second opening defined by the outer wall of the catheter member.
Figure 7:
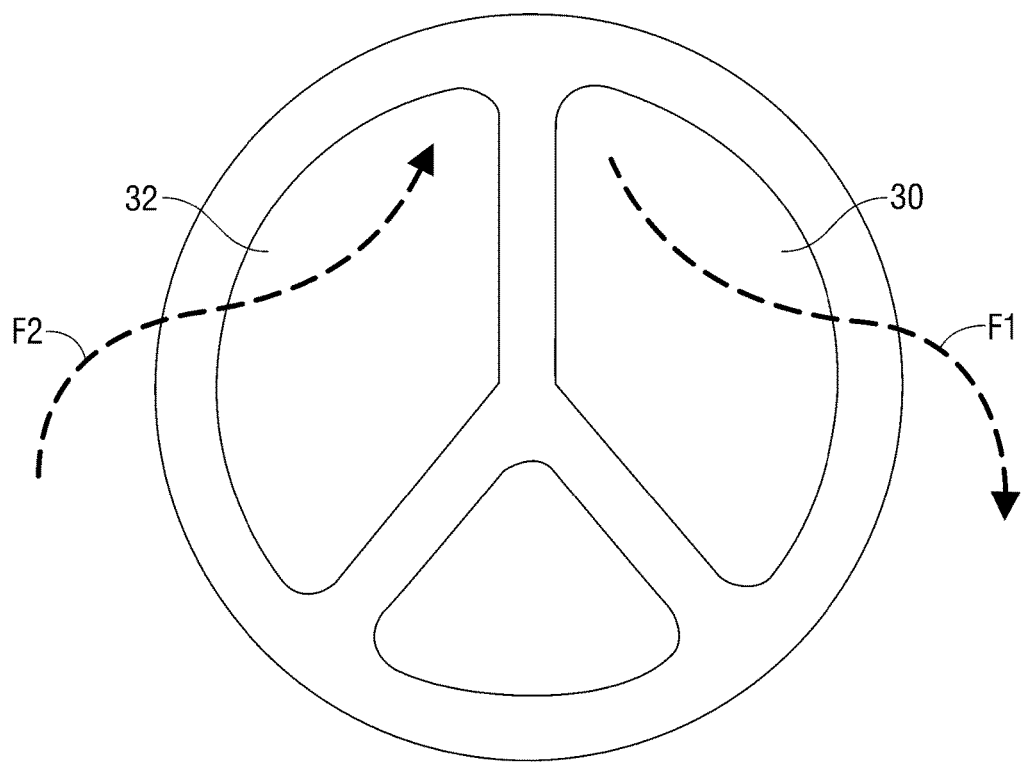
FIG. 7 is an end view of a distal portion of the catheter member.

The venous opening 42A is defined by a continuous wall 43A having first and second axial wall portions 44A, 46A (FIGS. 4, 6) extending along an axis parallel to the longitudinal axis "X" of the catheter member 14, as well as first and second transverse wall portions 48A, 50A which connect the first and second axial wall portions 44A, 46A. The dimensions of the axial wall portions 44A, 46A and the transverse wall portions 48A, 50A are such that the two-dimensional area defined by the venous opening 42A is greater than or equal to the cross-sectional area of the venous lumen 30. As best seen in FIG. 6, the first axial wall portion 44A of the venous opening 42A defines an axial length "L1"

that is less than an axial length "L2" defined by the second axial wall portion 46A. Consequently, the wall portions 44A, 46A, 48A, 50A of the venous opening 42A cooperatively define a proximal tapered portion 52A, a distal tapered portion 54A, and an intermediate portion 56A positioned therebetween. Specifically, the proximal tapered portion 52A is tapered such that a transverse dimensional thereof, i.e., a dimension measured along the circumference of the catheter body 14, increases in a distal direction. Oppositely, the distal tapered portion 54A is tapered such that a transverse dimension thereof, which is represented by the reference character β1, decreases in the distal direction. In contrast to the variable transverse dimensions α1, β1 of the proximal and distal tapered portions 52A, 54A, respectively, the intermediate portion 56A connecting the proximal tapered portion 52A and the distal tapered portion 54A includes a constant transverse dimension γ1.

In FIGS. 3-7, the transverse wall portions 48A, 50A of the venous opening 42A are each illustrated as including linear configurations, whereby the venous opening 42A is substantially trapezoidal in configuration. However, alternative embodiments of the catheter body 14 are also envisioned wherein either or both of the transverse wall portions 48A, 50A of the venous opening 42A may include an arcuate configuration. For example, it is envisioned that either or both of the transverse wall portion(s) 48A, 50A may be curved towards the first axial wall portion 44A, or away from the first axial wall portion 44A. Additionally, embodiments of the catheter body 14 are envisioned wherein one of the transverse wall portions 48A, 50A includes a linear configuration and the other includes an arcuate configuration.

Figure 4:
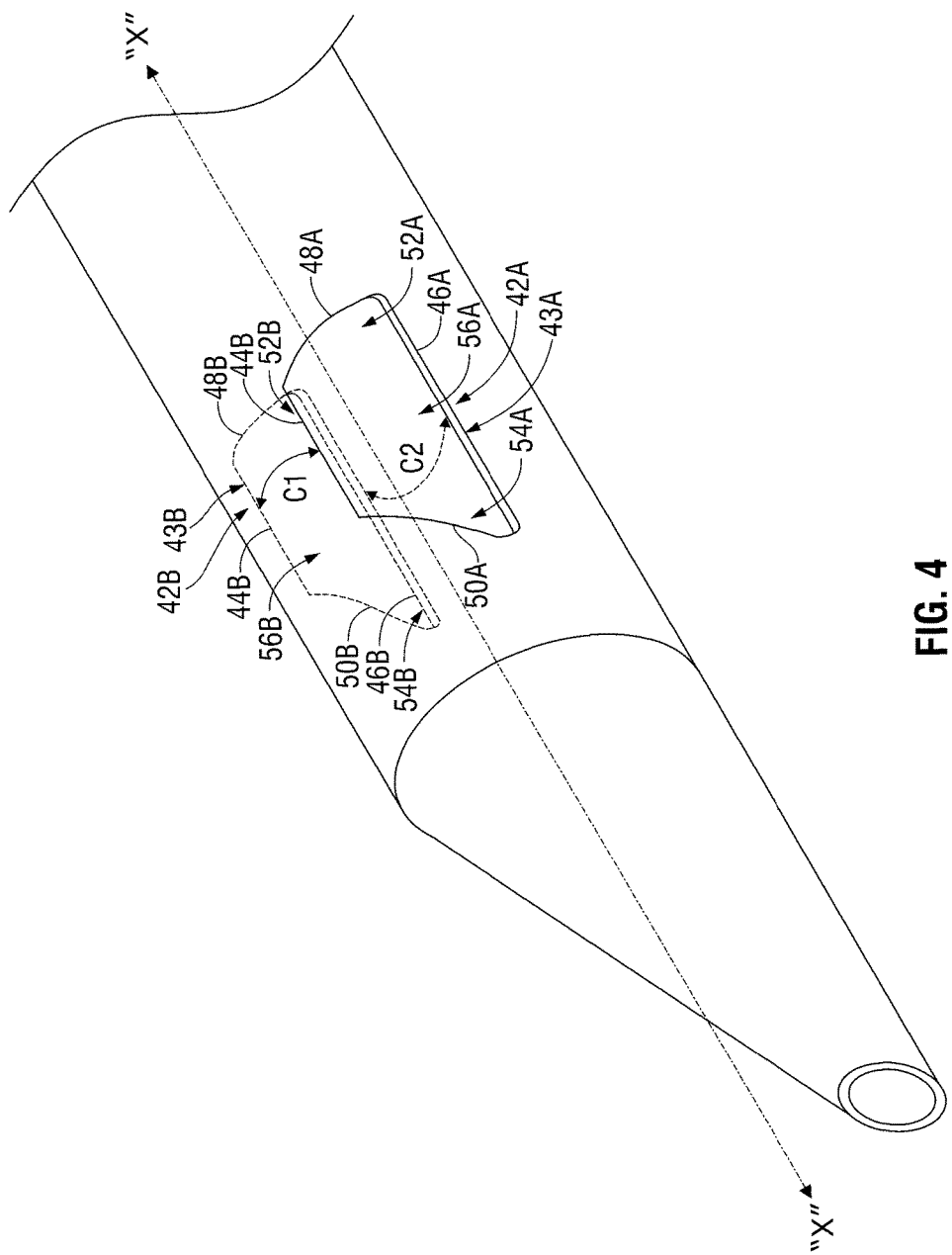
FIG. 4 is a side, perspective view of the area of detail indicated in FIG. 3.
Figure 5:
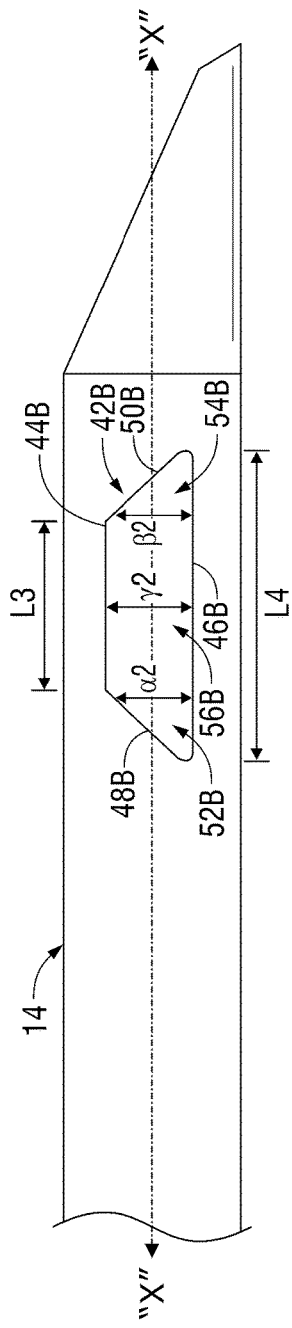
FIG. 5 is a side, plan view of a distal portion of the catheter member illustrating a first opening defined by an outer wall of the catheter member.

Referring now to FIGS. 4 and 5 in particular, the arterial opening 42B is defined by a continuous wall 43B having first and second axial wall portions 44B, 46B extending along an axis parallel to the longitudinal axis "X" of the catheter member 14, as well as first and second transverse wall portions 48B, 50B which connect the first and second axial wall portions 44B, 46B. The dimensions of the axial wall portions 44B, 46B and the transverse wall portions 48B, 50B are such that the two-dimensional area defined by the arterial opening 42B is greater than or equal to the cross-sectional area of the arterial lumen 32. As best seen in FIG. 5, the first axial wall portion 44B of the arterial opening 42B defines an axial length "L3" that is less than an axial length "L4" defined by the second axial wall portion 46B. Consequently, the wall portions 44B, 46B, 48B, 50B of the arterial opening 42B cooperatively define a proximal tapered portion 44B, a distal tapered portion 46B, and an intermediate portion 48B positioned therebetween. Specifically, the proximal tapered portion 52B is tapered such that a transverse dimension α2 thereof, i.e., a dimension measured along the circumference of the catheter body 14, increases in a distal direction. Oppositely, the distal tapered portion 54B is tapered such that a transverse dimension thereof, which is represented by the reference character β2, decreases in the distal direction. As with the venous opening 42A, whereas the proximal and distal tapered portions 52B, 54B of the arterial opening 42B include variable transverse dimensions α2, β2, respectively, the intermediate portion 56B connecting the proximal tapered portion 52B and the distal tapered portion 54B includes a constant transverse dimension γ2.

In FIGS. 3-7, the transverse wall portions 48B, 50B of the arterial opening 42B are each illustrated as including linear configurations, whereby the arterial opening 42B is substantially trapezoidal in configuration. However, alternative embodiments of the catheter body 14 are also envisioned wherein either or both of the transverse wall portions 48B, 50B of the arterial opening 42B may include an arcuate configuration. For example, it is envisioned that either or both of the transverse wall portion(s) 48B, 50B may be curved towards the first axial wall portion 44B, or away from the first axial wall portion 44B. Additionally, embodiments of the catheter body 14 are envisioned wherein one of the transverse wall portions 48B, 50B includes a linear configuration and the other includes an arcuate configuration.

While the catheter member 14 is illustrated as including venous and arterial openings 42A, 42B that are identical in configuration and dimensions throughout the FIGURES, an embodiment in which the structure of the venous opening 42A differs from that of the arterial opening 42B is not beyond the scope of the present disclosure.

With particular reference now to FIG. 4, the first axial wall portion 44A of the venous opening 42A is spaced a first distance "C1" along the circumference of the catheter body 14 from the first axial wall portion 44B of the arterial opening 42B, and the second axial wall portion 46A of the venous opening 42A is spaced a second distance "C2" along the circumference of the catheter body 14 from the second axial wall portion 46B of the arterial opening 42B. In the embodiment of the catheter body 14 illustrated in FIG. 4, the venous and arterial openings 42A, 42B are positioned in diametrical, opposed relation to maximize the distance therebetween. Stated differently, the venous and arterial openings 42A, 42B are positioned in the outer wall 28 such that the first distance "C1" is substantially equal to the second distance "C2." In alternative embodiments of the catheter body 14, however, it is envisioned that the respective first and second distances "C1" and "C2" may be unequal, e.g., that the first distance "C1" may be greater than second distance "C2," or that second distance "C2" may be greater than first distance "C1."

Referring now to FIGS. 1-7, the use and operation of the catheter assembly 10 will be discussed during the course of a hemodialysis procedure. Initially, a hollow needle cannula (not shown) is inserted into the target body vessel to create a venotomy (entry) site. For example, the needle cannula may be disposed within the skin of the subject, adjacent the neck and clavicle, for accessing a vein. Upon positioning the needle cannula within the target vessel, a guidewire (not shown) is inserted through a proximal end of the needle cannula and tunneled through to a desired location within the body vessel. The needle cannula is then withdrawn, leaving a distal end of the guidewire positioned within the target vessel, and a proximal end of the guidewire extending outwardly from the patient's body.

Following placement, the guidewire is inserted into the guidewire channel 36 extending through the catheter member 14 to facilitate distal advancement of the catheter member 14 into the target vessel. As is conventional in the art, it is envisioned that placement of the catheter member 14 may be assisted through the use of an insertion stylet and/or an introducer sheath.

As discussed above, in the embodiment of the catheter member 14 illustrated in FIGS. 1-7, the opening 42A is in fluid communication with the venous lumen 30 (FIG. 2), whereby a first flow stream, which is identified by the reference character "F1" (FIG. 7), is established, and the opening 42B is in fluid communication with the arterial lumen 32 (FIG. 2), whereby a second flow stream, which is identified by the reference character "F2" (FIG. 7), is established. Accordingly, fluid, e.g., blood, exiting the catheter member 14 will follow the path of the first flow stream "F1" out of the venous lumen 30 through the opening 42A, and blood entering the catheter member 14 will follow the path of the second flow stream "F2" into the arterial lumen 32 through the opening 42B.

Due to the inertial force of the blood flowing into and out of the catheter member 14, the flowing blood will exhibit a general tendency to stay in motion, and will typically follow the path of least resistance. Consequently, blood exiting the venous lumen 30 (FIG. 2) will generally flow past the proximal tapered portion 52A (FIGS. 4, 6) of the opening 42A and out of the catheter member 14 via the distal tapered portion 54A, and blood entering the arterial lumen 32 (FIG. 2) will generally flow past the distal tapered portion 54B (FIGS. 4, 5) of the opening 42B and into the catheter member 14 via the proximal tapered portion 52B. Thus, the distal tapered portion 54A of the venous opening 42A and the proximal tapered portion 52B of the arterial opening 42B will constitute high-flow zones during the communication of blood into and out of the catheter member 14 where the velocity of flowing blood, and the pressure exerted thereby, is the highest.

The substantially trapezoidal configuration of the venous opening 42A (FIGS. 4, 6) and the arterial opening 42B (FIGS. 4, 5) targets and directs blood flow into these high-flow zones, and increases the axial and circumferential spacing between the high-flow zones, when compared to alternative configurations. For example, by positioning the respective venous and arterial openings 42A, 42B at substantially the same axial location along the longitudinal axis "X" (FIG. 4) of the catheter member 14, and by spacing the respective venous and arterial openings 42A, 42B equidistant from each other about the circumference of the catheter member 14, the openings 42A, 42B cooperate to optimize the axial and circumferential spacing between the high-flow zones, thereby minimizing the likelihood of occlusion, and limiting recirculation. Additionally, the trapezoidal configuration of the respective venous and arterial openings 42A, 42B has been found to optimize both the perimeter of the openings 42A, 42B, as well as the circumferential height thereof, when compared to alternative, known configurations employed in the art.

In various embodiments of the present disclosure, it is envisioned that the circumferential and axial distances between the high-flow zones of the venous opening 42A (FIGS. 4, 6) and the arterial opening 42B (FIGS. 4, 5) may be varied. By varying the circumferential and axial distances between the high-flow zones of the respective venous and arterial openings 42A, 42B, the tendency of the blood to flow past the proximal tapered portion 52A (FIGS. 4, 6) of the venous opening 42A such that the blood exits the venous lumen 30 (FIG. 2) via the distal tapered portion 54A will be increased, as will the tendency of the blood to flow past the distal tapered portion 54B (FIGS. 4, 5) of the arterial opening 42B to enter the arterial lumen 32 (FIG. 2) via the proximal tapered portion 52B. Consequently, by varying the circumferential and axial distances between the high-flow zones of the respective venous and arterial openings 42A, 42B, recirculation of the blood can be regulated and minimized, as well as the likelihood of positional occlusion, and/or fibrin sheath or thrombus formation.

Additionally, it is envisioned that the perimeter and/or circumferential height of the respective venous and arterial openings 42A, 42B may be varied in alternative embodiments of the present disclosure in order to further impact the tendency of flowing blood to exit the venous opening 42A (FIGS. 4, 6) via the distal tapered portion 54A, and enter the arterial opening 42B (FIGS. 4, 5) via the proximal tapered portion 52B in order to further impact recirculation, and/or the likelihood of positional occlusion, and/or fibrin sheath or thrombus formation.

Figure 8:
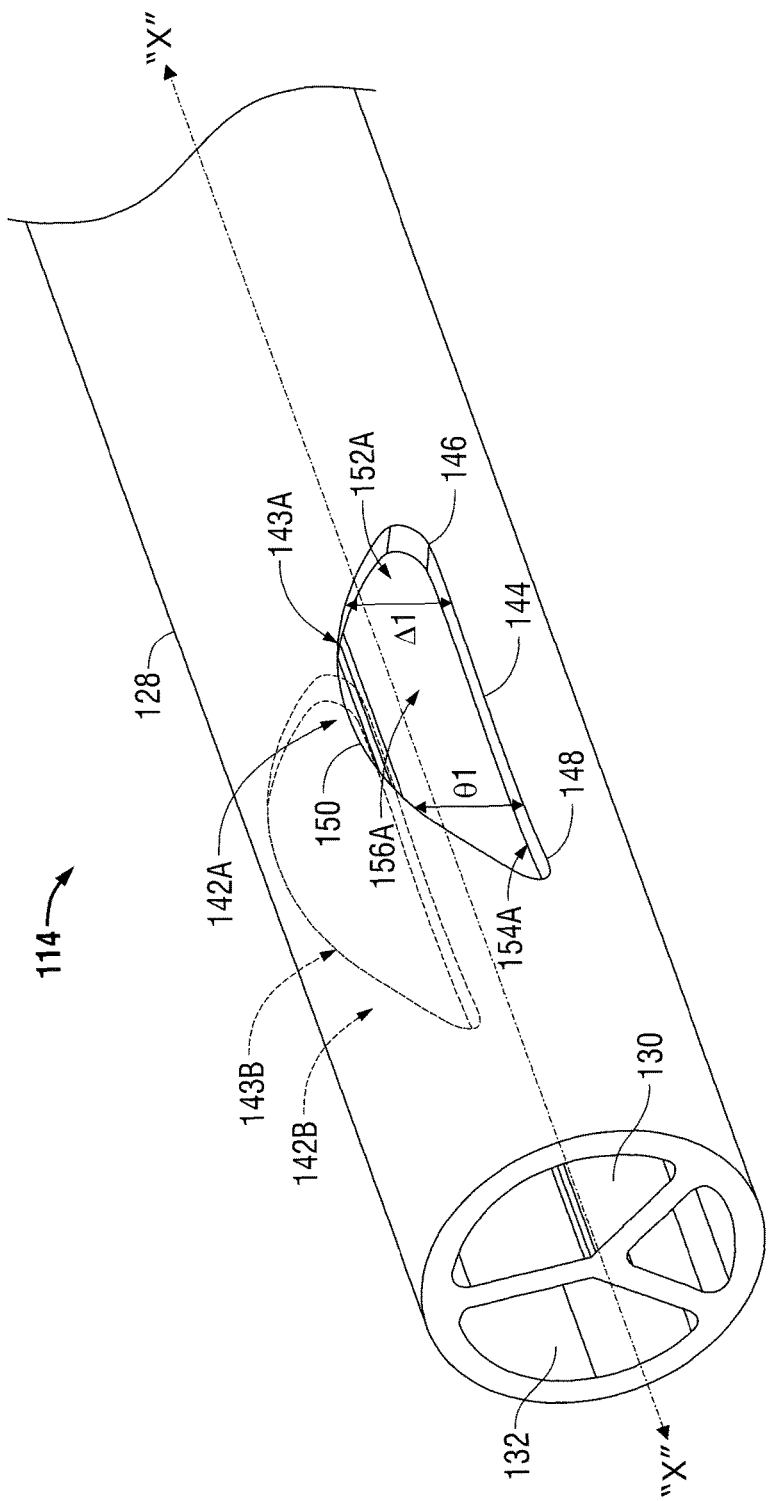
FIG. 8 is a side, perspective view of a distal portion of the presently disclosed catheter member including first and second openings according to an alternative embodiment of the present disclosure.

Referring now to FIG. 8, an alternative embodiment of the catheter member, referred to generally by reference character 114 will be discussed. The catheter member 114 is similar to the catheter member 14 discussed above with respect to FIGS. 1-7, and accordingly, will only be discussed with respect to any differences therebetween.

The catheter member 114 includes an outer wall 128 defining a first opening 142A and a second opening 142B. The first opening 142A is in fluid communication with a first internal lumen 130 extending through the catheter member 114 for the withdrawal of fluid from the patient, thus functioning as a arterial opening, and the second opening 142B is in fluid communication with a second internal lumen 132 extending through the catheter member 114 for the return of fluid to the patient, thus functioning as an venous opening.

The first opening 142A is defined by a continuous wall 143A having an axial wall portion 144 with proximal and distal ends 146, 148, respectively, and extending along an axis parallel to the longitudinal axis "X" of the catheter member 114. The wall 143A defining the first opening 142A further includes an arcuate wall portion 150 that connects the proximal end 146 of the axial wall portion 144 to the distal end 148. The dimensions of the axial wall portion 144 and the arcuate wall portion 150 are such that the two-dimensional area defined by the first opening 142A is greater than or equal to the cross-sectional area of the first internal lumen 130.

Figure 9:
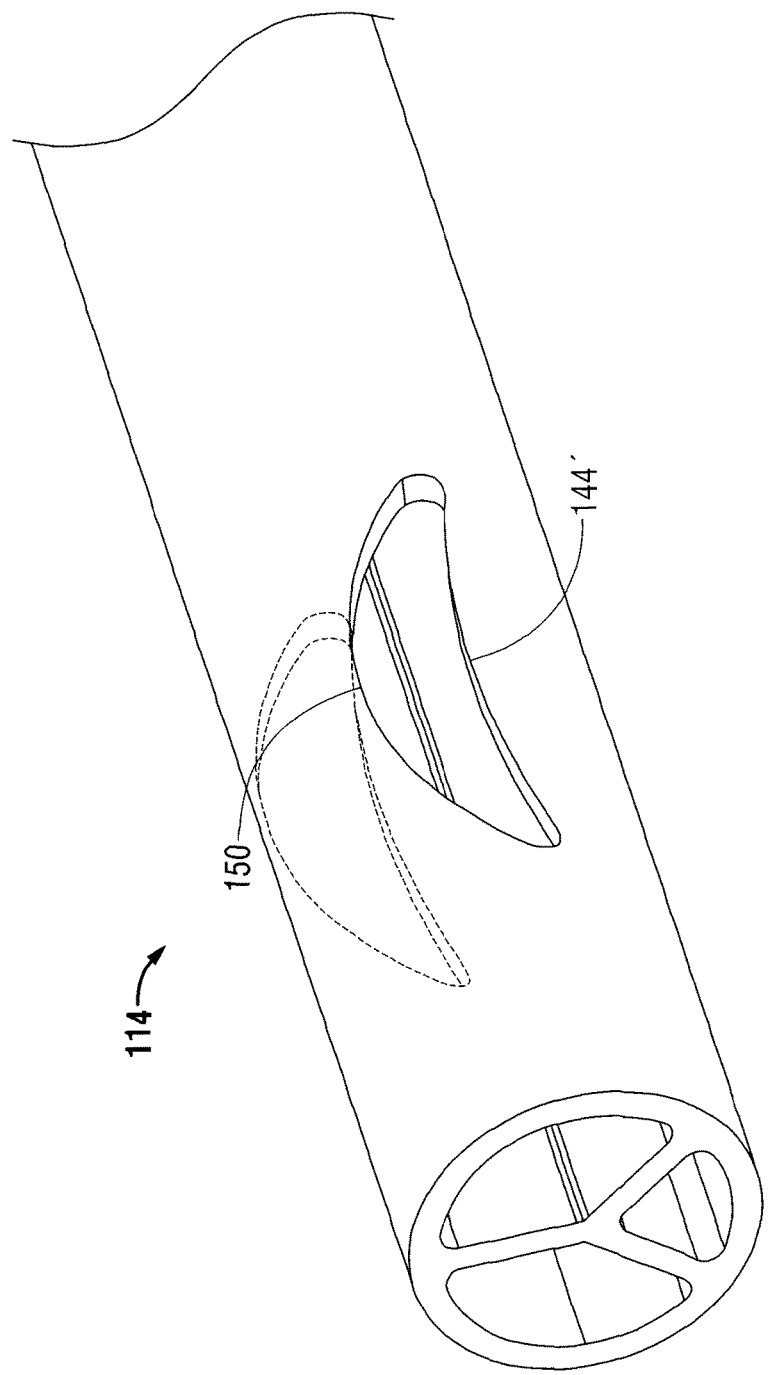
FIG. 9 is a side, perspective view of a distal portion of the presently disclosed catheter member including first and second openings according to another embodiment of the present disclosure.

Although illustrated as including a substantially linear configuration in the embodiment of the catheter member 114 illustrated in FIG. 8, it is envisioned that the configuration of the wall portion 144 may be varied in alternative embodiments, e.g., to alter the communication of fluid into the first opening 142A. For example, as illustrated in FIG. 9, in one embodiment, the catheter member 114 may include a wall portion 144' with an arcuate configuration, e.g., a configuration curving towards the arcuate wall portion 150. It is also contemplated, however, that the configuration of the wall portion 148' may alternatively curve away from the arcuate wall portion 150.

Referring again to FIG. 8, the curvature of the of the arcuate wall portion 150 is such that the first opening 142A includes a proximal tapered portion 152A, a distal tapered portion 154A, and an intermediate portion 156A positioned therebetween. Specifically, the proximal tapered portion 152A is tapered such that a transverse dimension Δ1 thereof, i.e., a dimension measured along the circumference of the catheter body 14, increases in a distal direction. Oppositely, the distal tapered portion 154A is tapered such that a transverse dimension thereof, which is represented by the reference character θ1, decreases in the distal direction.

In the embodiment of the catheter 114 illustrated in FIG. 8, the second opening 142B is substantially identical in both configuration and dimensions to the first opening 142A. Thus, in the interests of brevity, the second opening 142B will not be discussed in detail.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the invention based on the above-described embodiments. For example, the catheter member 14 (FIG. 1) may include at least one cuff (not shown) on the outer wall 28 to function as a site for tissue ingrowth for long term securing of catheter assembly 10 in an indwelling position, and or radiopaque markings or strips (not shown) to facilitate the location of catheter member 14 within the patient's tissue with a fluoroscope. Accordingly, the invention is not to be limited by what has been particularly shown and described, except as indicated by the appended claims.

What is claimed is:

1. A medical catheter assembly, comprising:
an elongate catheter member defining a longitudinal axis and having a proximal end, a distal end, and an outer wall, the elongate catheter member defining first and second internal lumens extending therethrough, the outer wall defining a first opening in fluid communication with the first internal lumen to facilitate establishment of a first flow stream, and a second opening in fluid communication with the second internal lumen to facilitate establishment of a second flow stream, the first and second openings each including proximal and distal tapered portions connected by an intermediate portion extending longitudinally between the proximal and distal tapered portions and having a constant dimension transverse to the longitudinal axis, whereby separation of the first flow stream from the second flow stream is maximized to reduce the likelihood of recirculation between the first and second internal lumens.

2. The medical catheter assembly of claim 1, wherein the proximal tapered portions of the first and second openings include a transverse dimension that increases in a distal direction.

3. The medical catheter assembly of claim 1, wherein the distal tapered portions of the first and second openings include a transverse dimension that decreases in a distal direction.

4. The medical catheter assembly of claim 1, wherein the first opening is defined by a first continuous wall, and the second opening is defined by a second continuous wall, the first and second walls each having first and second axial wall portions extending along an axis parallel to the longitudinal axis, and first and second transverse wall portions connecting the first and second axial wall portions.

5. The medical catheter assembly of claim 4, wherein the first axial wall portions define a first length and the second axial wall portions define a second, greater length.

6. The medical catheter assembly of claim 4, wherein at least one of the first and second transverse wall portions includes an arcuate configuration.

7. The medical catheter assembly of claim 6, wherein at least one of the first and second transverse wall portions includes an arcuate configuration curving towards the second axial wall portion.

8. The medical catheter assembly of claim 4, wherein each of the first and second transverse wall portions includes an arcuate configuration.

9. The medical catheter assembly of claim 8, wherein each of the first and second transverse wall portions includes an arcuate configuration curving towards the second axial wall portion.

10. The medical catheter assembly of claim 1, wherein the first and second openings are identical in configuration and dimensions.

11. The medical catheter assembly of claim 4, wherein the first axial wall portions define a first distance therebetween measured along a circumference of the elongate catheter member, and the second axial wall portions define a second distance therebetween measured along a circumference of the elongate catheter member, the first distance and the second distance being equal to thereby maximize separation of the first and second openings.

12. The medical catheter assembly of claim 1, further including a third internal lumen extending therethrough, wherein the first, second, and third internal lumens are separated by at least two septums extending inwardly from the outer wall.

13. A medical catheter assembly, comprising:
an elongate catheter member extending along a longitudinal axis and having a proximal end, a distal end, and an outer wall, the elongate catheter member defining a first internal lumen and a second internal lumen, the outer wall defining a first opening in fluid communication with the first internal lumen to facilitate establishment of a first flow stream, and a second opening in fluid communication with the second internal lumen to facilitate establishment of a second flow stream, wherein the first opening is defined by a first continuous wall having first and second transversely spaced axial wall portions, and the second opening is defined by a second continuous wall having first and second transversely spaced axial wall portions, the first axial wall portions and the second axial wall portions defining an equivalent distance therebetween measured along a circumference of the elongate catheter member to thereby maximize separation of the first and second openings, whereby separation of the first flow stream from the second flow stream is maximized to reduce the likelihood of recirculation between the first and second internal lumens.

14. The medical catheter assembly of claim 13, wherein the first axial wall portions define a first length and the second axial wall portions define a second, greater length.

15. The medical catheter assembly of claim 13, wherein the first and second openings are identical in configuration and dimensions.

16. The medical catheter assembly of claim 13, wherein the first and second axial wall portions of the first wall are connected by a pair of first transverse wall portions, and the first and second axial wall portions of the second wall are connected by a pair of second transverse wall portions.

17. The medical catheter assembly of claim 16, wherein at least one of the pairs of the first and second transverse wall portions has an arcuate configuration.

18. The medical catheter assembly of claim 16, wherein the first and second openings each include proximal and distal tapered portions connected by an intermediate portion having a constant transverse dimension.

19. The medical catheter assembly of claim 16, wherein the proximal tapered portions of the first and second openings have a transverse dimension that increases in a distal direction.

20. The medical catheter assembly of claim 16, wherein the distal tapered portions of the first and second openings have a transverse dimension that decreases in a distal direction.

* * * * *